United States Patent [19]
Cole et al.

[11] Patent Number: 6,059,765
[45] Date of Patent: May 9, 2000

[54] FLUID MANAGEMENT SYSTEM WITH VERTEX CHAMBER

[75] Inventors: Mark S. Cole, Trabuco Canyon; Tom Sutton, Huntington Beach, both of Calif.

[73] Assignee: Allergan Sales, Inc., Irvine, Calif.

[21] Appl. No.: 09/031,101

[22] Filed: Feb. 26, 1998

[51] Int. Cl.[7] .................................................. A61M 29/00
[52] U.S. Cl. ............................. 604/500; 604/30; 604/35; 604/118
[58] Field of Search ................................ 604/27, 30, 35, 604/34, 43, 118, 93, 246, 250, 131, 500; 128/DIG. 13; 417/313, 478; 600/485, 488; 73/715–717, 723

[56] References Cited

U.S. PATENT DOCUMENTS

| | | | |
|---|---|---|---|
| 4,369,785 | 1/1983 | Rehkopf et al. | 128/276 |
| 4,425,116 | 1/1984 | Bilstad et al. | 604/34 |
| 4,475,904 | 10/1984 | Wang | 604/119 |
| 4,479,761 | 10/1984 | Bilstad et al. | 417/395 |
| 4,627,833 | 12/1986 | Cook | 604/34 |
| 4,713,051 | 12/1987 | Steppe et al. | 604/33 |
| 4,735,610 | 4/1988 | Akkas et al. | 604/119 |
| 4,798,580 | 1/1989 | DeMeo et al. | 604/30 |
| 4,904,168 | 2/1990 | Cavoto et al. | 417/477 |
| 4,921,477 | 5/1990 | Davis | 604/22 |
| 4,963,131 | 10/1990 | Wortrich | 604/34 |
| 5,106,366 | 4/1992 | Steppe | 604/30 |
| 5,470,312 | 11/1995 | Zanger et al. | 604/34 |

FOREIGN PATENT DOCUMENTS

| | | |
|---|---|---|
| 0293081 | 11/1988 | European Pat. Off. . |
| 0559602 | 9/1993 | European Pat. Off. . |
| 37 05 266 A1 | 2/1987 | Germany . |
| WO 8607249 | 12/1986 | WIPO . |

*Primary Examiner*—Corrine McDermott
*Assistant Examiner*—Michael J. Hayes
*Attorney, Agent, or Firm*—Walter A. Hackler

[57] ABSTRACT

Fluid management apparatus for a surgical instrument having fluid irrigation and aspiration lines includes a console having an aspiration pump and housing having a longitudinal axis. A chamber is disposed in the housing having an aspiration fluid inlet and aspiration fluid outlet, with the outlet being disposed along the longitudinal axis and connected to the aspiration pump. A frame is proved for engaging and holding the housing of the console with a longitudinal axis in a generally vertical orientation for preventing accumulation of gas within the chamber. In addition, a chamber inlet is disposed along a chamber perimeter in order to cause circulation of introduced fluid within the chamber to inhibit settling of particulate material within the chamber.

19 Claims, 3 Drawing Sheets

FLUID MANAGEMENT SYSTEM WITH VERTEX CHAMBER

The present invention generally relates to irrigation/aspiration apparatus for surgical procedures and more particularly relates to fluid management apparatus for use with a surgical instrument for endophthalmic surgery.

The removal of cataracts, for example, involves surgery on a normally pressurized eye in which instruments are passed through a small incision at the edge of the cornea in order to access and remove opaque cataract material.

The cataracts may be fragmentized by cutting apparatus, vibratory apparatus, or the like, and the fragments are aspirated from the eye.

In order to maintain normal pressure within the eye, a balanced salt solution is supplied from an elevated chamber, the chamber being elevated to a position to provide proper head, or pressure.

The irrigation and aspiration of fluid through the eye must be carefully monitored and controlled in order to maintain normal pressure within the eye during surgical procedures. An under-pressure may cause distortion of the eye which often may interfere with surgical procedures. Over pressure may cause damage to the eye and in extreme cases, rupture thereof.

As it has been hereinabove noted, pressure in the eye may be controlled by the physical elevation of the chamber of balanced salt solution, which is connected to the surgical instrument. Aspiration fluid, on the other hand, is typically controlled in the eye with a peristaltic pump or the like.

Conventional apparatus includes an instrument console for controlling the flow of fluids. Various devices have been developed for the coordinated flow of fluids and some include a phacocassette, or tubing and management system, which may be disposable or autoclavable, for interconnecting from the various tubes and lines for proper irrigation and aspiration.

A general discussion of the advantages of this type of cassette is set forth in U.S. Pat. No. 4,713,051, which teaches a housing for supporting a portion of irrigation and aspiration tubing, together with a drain bag structured so that all fluid and connections are precisely made to a console by insertion of the cassette thereinto. Thus, the reliability of the fluid connections is enhanced.

Other fluid management apparatus for control of irrigation and aspiration fluid as well as cassettes therefor are discussed in U.S. Pat. Nos. 4,425,116; 4,475,904; 4,479,761; 4,627,833; 4,735,610; 4,798,580; 4,904,168; 4,963,131; 5,106,366 and 5,470,312.

The last hereinabove referenced U.S. patent, namely, U.S. Pat. No. 5,470,312, teaches a chamber and diaphragm arrangement for improving response time to pressure variations in an aspiration line while a surgical instrument and is incorporated herewith entirely by this specific reference thereto for also teaching the use of a chamber and diaphragm for measuring pressure in an aspiration line.

Differential pressure in an aspiration line can be caused by fragments broken tissue which temporarily block the aspiration line. This differential pressure is typically accommodated by ceasing or slowing the aspirational flow through the regulation of a peristaltic pump, or the like, connected to the aspiration line.

As discussed in U.S. Pat. No. 5,470,312, during aspiration, particles may restrict the aspiration flow from the eye and accordingly vacuum levels are increased to create a greater differential pressure across the occluding particle and effort to move the particle downstream and away from the eye. Typically, particles require much higher force to start movement than it takes to continue movement.

Once a particle moves, it creates a volume of fluid behind it to take up the space once occupied. This volume may momentarily be larger than the volume of the eye, therefore, producing a momentary dimpling of the eye. The pressure sensing of this condition is well within the operation of typical phaco machines; however, the response to this condition is typically slow. Accordingly, a solenoid activated diaphragm, is taught in the U.S. Pat. No. 5,470,312, may be utilized to improve the response time.

However, this apparatus provides no accommodation for expandable gases which are in the aspiration line. It should be easily appreciated that the vacuum-rise time for a vacuum generation system, such as, for example, a peristaltic pump, is much faster without expandable gases in the system. Accordingly, the generation of pressure in a pressure building system is much faster without compressible gases in the system.

Hence, it is preferable to remove expandable gas in the aspiration line in order to improve the fluidic surge after clearing of an aspiration line of occlusion.

The present invention provides apparatus and method for reducing expandable gas in the aspiration line of a fluid management system for a surgical instrument.

SUMMARY OF THE INVENTION

Fluid management apparatus in accordance with the present invention for use with a surgical instrument having fluid irrigation and aspiration lines generally includes a console having an aspiration pump and a separate housing which includes a chamber disposed therein having an aspiration fluid inlet and an aspiration fluid outlet. The aspiration fluid outlet is disposed along a housing longitudinal axis and is connected to the aspiration pump.

Means are provided for preventing an accumulation of gases, either generated in or introduced into the chamber, in the chamber. This is achieved by holding the housing to the console with the longitudinal access in a generally vertical orientation, with the aspiration fluid outlet being disposed below the pump. In this manner any expandable gases present in the chamber rise toward the outlet and pump so that when fluid flow is temporarily stopped, no accumulation of gases occurs in the chamber. Thus accumulated gas which may otherwise slow the vacuum rise time upon recommencement of aspiration by the peristaltic pump is eliminated.

More particularly, the aspiration fluid inlet is disposed on an opposite side of the chamber and, further, the inlet is disposed and arranged along the chamber perimeter for causing circulation of the introduced fluid within the chamber in order to inhibit settling of particulate material in the introduced fluid in the chamber. To enhance this circulation, preferably the chamber has a generally circular shape and more particularly may have a toroidal shape. A diaphragm may be utilized, enclosing one side of the chamber, as a means for enabling measurement of pressure of the fluid in the chamber.

Another embodiment of the present invention includes the hereinabove referenced housing taken in combination with means, disposed in the console, for engaging and holding the housing with the longitudinal access thereof in a general vertical orientation.

BRIEF DESCRIPTION OF THE DRAWINGS

The advantages and features of the present invention will be better understood by the following description when considered in conjunction with the accompanying drawings, in which.

DETAILED DESCRIPTION

Figure 1:
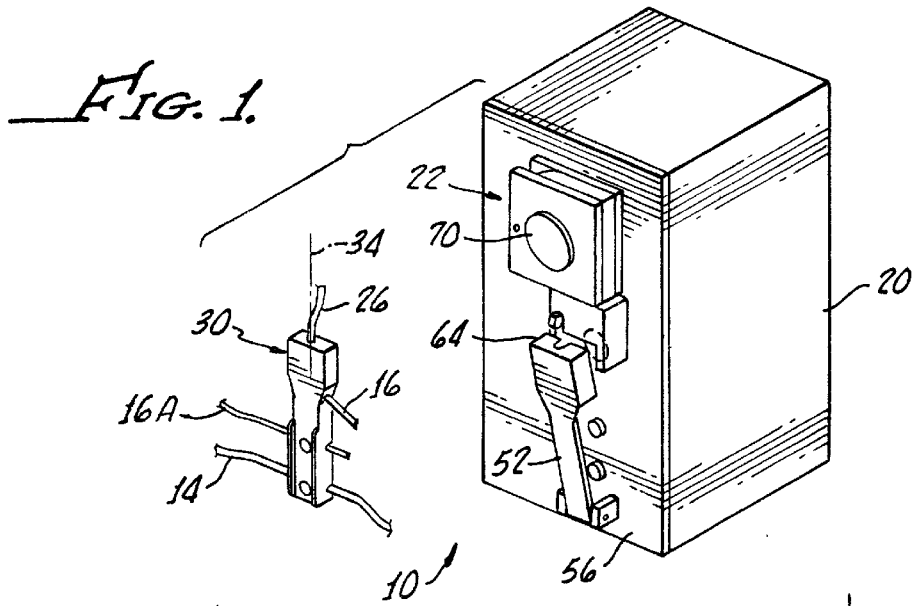
FIG. 1 is a perspective view of fluid management apparatus in accordance with the present invention generally showing a console and a housing suitable for insertion therein for controlling irrigation and aspiration of fluids to a handpiece, not shown.

Turning now to FIG. 1, there is shown fluid management apparatus 10 in accordance with the present invention for a surgical instrument (not shown) having a fluid irrigation line 14, a fluid aspiration line 16, fluid vent line 16A.

Generally, the apparatus 10 includes a console 20 having an aspiration pump 22 for engaging an aspiration fluid outlet line connected to a housing 30 as hereinafter described in greater detail.

Figure 2:
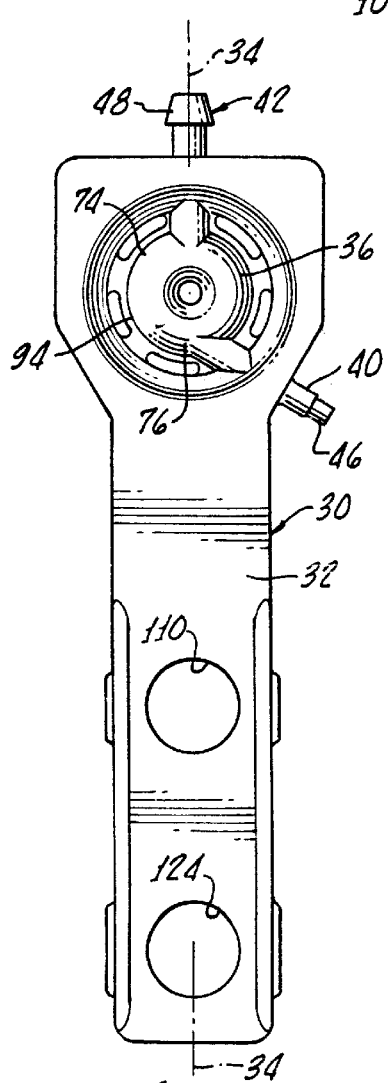
FIG. 2 is a front plan view of the housing shown in FIG. 1 generally showing a chamber along with a chamber inlet and chamber outlet.
Figure 3:
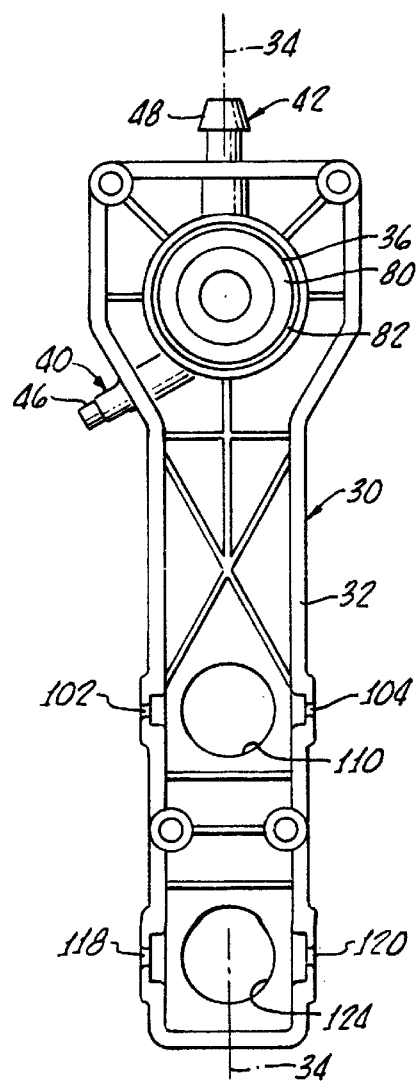
FIG. 3 is a plan view of a reverse side of the housing shown in FIG. 2, more specifically showing the chamber.

As more clearly shown in FIGS. 2 and 3, the housing 30 includes a molded elongate frame 32 having a longitudinal axis 34 with a chamber 36 preferably formed therein by conventional molding techniques.

As will be hereinafter described in greater detail, the chamber 36 includes an aspiration fluid inlet 40 and an aspiration fluid outlet 42. Each of the inlet and outlets 40, 42 include a suitable nipple 46, 48 for interconnection with conventional tubing, or lines, 16, 26.

As most clearly shown in FIG. 4, the console 20 includes a frame 52, hinge 54 mounted to a face 56 which provides a means for engaging and holding the housing 30 to the console 20, with the longitudinal axis 34 generally in a vertical orientation with the fluid outlet 42 disposed below the pump 22. A latch 62 engages a lip 64 on the frame 52 for locking the housing in the hereinabove noted vertical orientation. Thus, the frame in combination with the console 20 and housing 30 provides a means for preventing accumulation of gas (which may be generated or introduced into the chamber) from accumulating in the chamber 36 during operation of the pump 22. The pump 22 may be a peristaltic type of conventional design, draws fluid through the chamber 36 by the line 26. A suitable pump 22 is described in U.S. Pat. No. 5,230,614 and this patent is to be incorporated herewith by this specific reference thereto. However, during temporary pausing or slowing of aspiration fluid through the chamber 36, gas generated or introduced into the chamber, for example, by a change of pressure on the aspiration fluid, does not accumulate in the chamber, but rather rises through the chamber 36, because of its vertical orientation, and exits the chamber 36 through the outlet 42 and, of course, is passed to the pump 22 in view of the fact that the outlet 42 is disposed below the pump 22. Accordingly, as hereinabove noted, because no gas is present in the chamber 36, response time for achieving a desired aspiration rate is enhanced.

It should be appreciated that any conventional control system 68 with suitable display 70 can be used for controlling the pump 22.

Turning again to FIGS. 2 and 3, it is clear that the chamber inlet 40 is disposed on one side 74 of the chamber 36, while the inlet is disposed on an opposite side 76 of the chamber 36. Preferably, the chamber 36 has a generally circular shape and more preferably the chamber has a toroidal shape as shown in FIG. 2 and 3.

As shown in FIG. 3 a diaphragm 80 provides means for closing a back side of the chamber and enabling measurement of pressure within the chamber 36 of fluid introduced therein. When the housing 30 is secured to the console by the frame 52, the diaphragm is positioned to contact a magnetic pickup 88, such that movement of the diaphragm is translated into a pressure signal generated by a sensing system 90. The diaphragm and system 90 may be made in accordance with U.S. Pat. No. 5,470,312 or 5,649,905, both of which are incorporated herewith intoto for exemplifying a suitable diaphragm pressure sensing system, which may be used in the present invention.

Importantly, the chamber inlet 40 is oriented along a chamber perimeter 94 for causing circulation introduced fluid within the chamber 36 in order to inhibit settling of particulate matter, carried by the introduced fluid, into the chamber 36, thus a circular pattern of fluid is established within the chamber 36 which maintains a suspension of particulate material in the introduced fluid until it is evacuated by the pump 22 through the outlet 42 in line 26.

Figure 5:
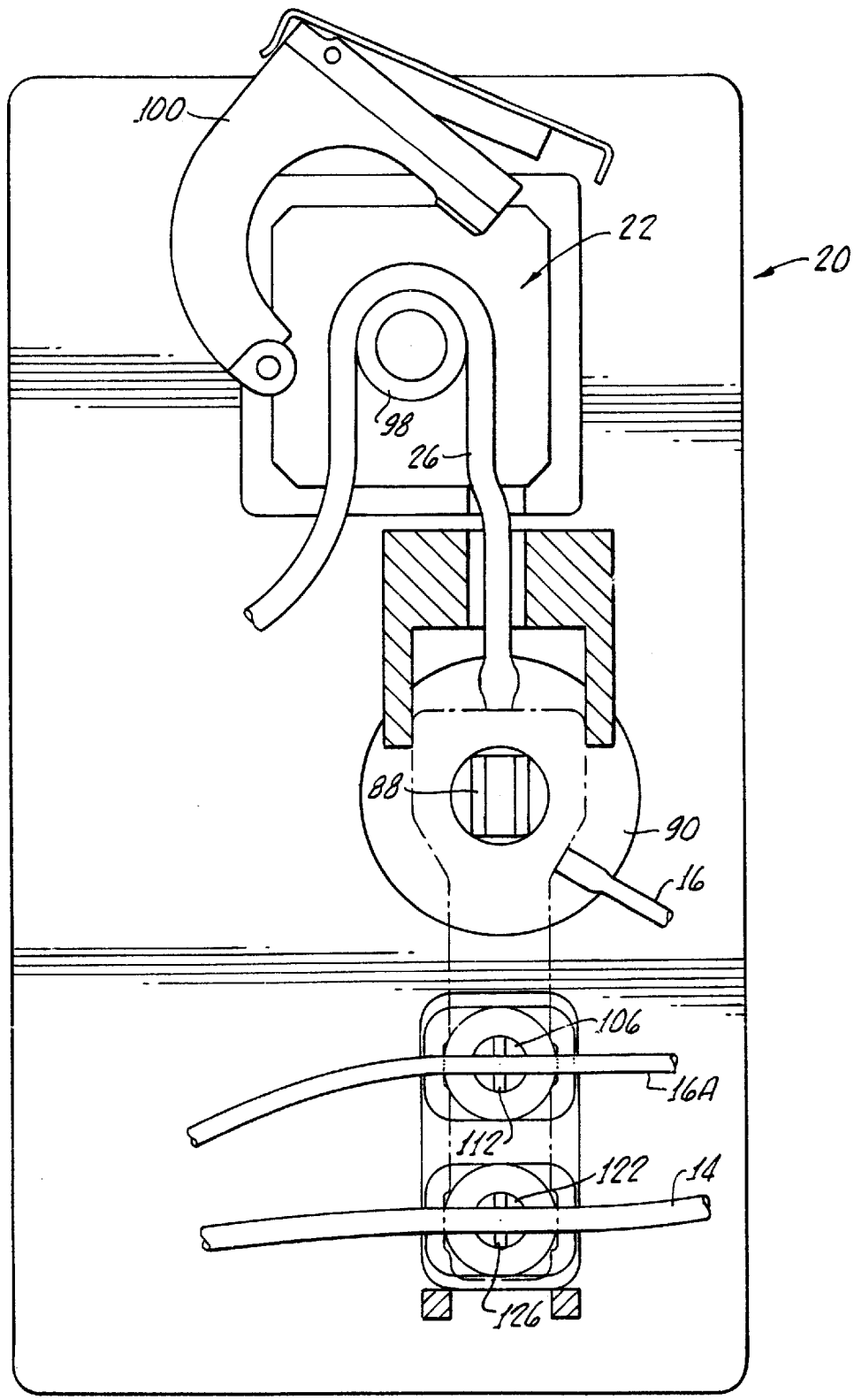
FIG. 5 is a front plan view of the console shown in FIG. 4.

As shown in FIG. 5, the line 26 from the chamber outlet 42 is wrapped around a pump head 98 and secured in an operable position by a conventional closure 100. The peristaltic pump 22 works in a conventional manner for causing aspiration of fluid from the chamber 36 via the line 26.

The chamber inlet 40 is connected to a line 16. The vent line is held in the housing 13 by slots 102, 104, for suspending a portion 106 across an opening 110 for access by a plunger 112 actuated by a solenoid or the like 114 (see FIG. 4). The plunger 112 and solenoid arrangement 114 for controlling fluid flow through the tubing 16A, being conventional in nature.

Figure 4:
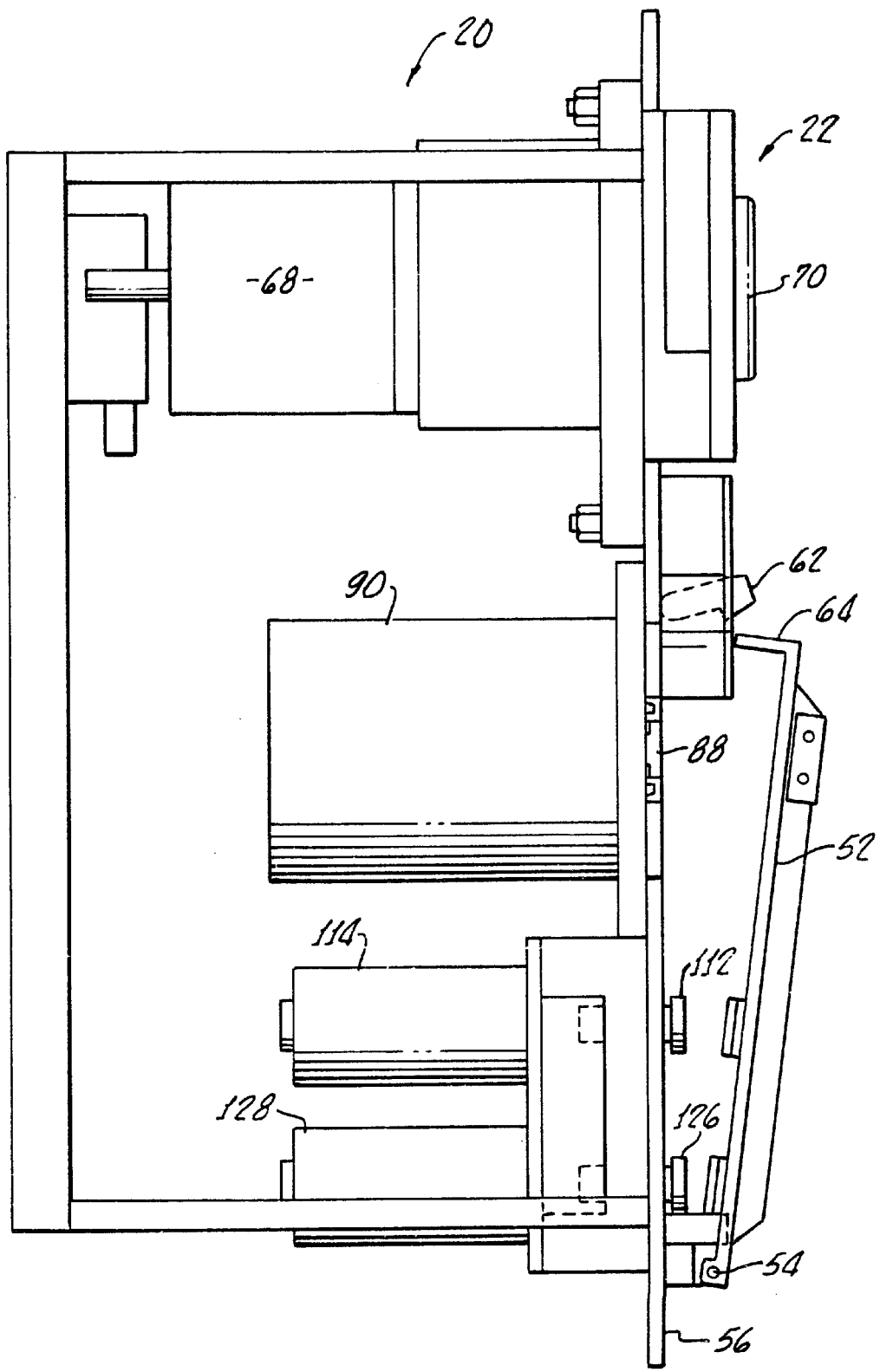
FIG. 4 is a side view of the console shown in FIG. 1 generally showing means for engaging and holding the housing to the console in a generally vertical orientation.

A similar arrangement is provided for the irrigation, line 14, in which slots 118, 120 (see FIG. 3) suspend a portion 22 of the tube over an opening 124 in the housing 30 in operative relationship with a plunger 126 controlled by a solenoid 128 (see FIG. 4). Again, this plunger solenoid tubing arrangement is well known in the art. For example, U.S. Pat. No. 5,470,312 shows and describes in U.S. Pat. No. 5,470,312 suitable for use in accordance with the present invention. This reference is to be incorporated herewith describing suitable tubing/plunger arrangements for controlling fluid flow in the irrigation and vent lines 14, 16A.

Although there has been described hereinabove a specific embodiment of fluid management apparatus in accordance with the present invention, for the purpose of illustrating the manner in which the invention may be used to advantage, it should be appreciated that the invention is not limited thereto. Accordingly, any and all modifications, variations, equivalent arrangements which may occur to those skilled in the art should be considered to be within the scope of the present invention as defined in the appended claims.

What is claimed is:

1. Fluid management apparatus for a surgical instrument having fluid irrigation and aspiration lines, said fluid management apparatus comprising:

a console having an aspiration pump;

a housing having a longitudinal axis;

a chamber, disposed in said housing, having an aspiration fluid inlet and an aspiration fluid outlet, the outlet being disposed along the housing longitudinal axis and connected to said aspiration pump; and means for preventing accumulation of gas, generated in or introduced into the chamber, in said chamber, said means for preventing accumulation of gas comprises:

means, disposed in said console, for engaging and holding said housing to the console with the longitudinal axis in a generally vertical orientation with the fluid outlet disposed below the pump; and chamber shape means for directing rising gas, within the vertically oriented chamber, toward said aspiration fluid outlet.

2. The apparatus according to claim 1 wherein the chamber inlet and chamber outlet are disposed on opposite sides of said chamber.

3. The apparatus according to claim 2 wherein said chamber has a perimeter and the apparatus further comprises means, orienting said chamber inlet along the chamber perimeter, for causing circulation of the introduced fluid within said chamber in order to inhibit settling of particulate material, in the introduced fluid, in said chamber.

4. The apparatus according to claim 3 wherein said chamber has a generally circular shape.

5. The apparatus according to claim 4 further comprising diaphragm means, closing one side of said chamber, for enabling measurement of pressure of the introduced fluid.

6. The apparatus according to claim 3 wherein said chamber has a toroidal shape.

7. Fluid management apparatus for use with a surgical console for providing irrigation and aspiration of fluids through irrigation and aspiration lines, respectively, said surgical console having a fluid aspiration pump, said fluid management apparatus comprising:

a housing having a longitudinal axis and a chamber formed therein;

chamber inlet means, adapted for connection to the aspiration line, for introducing aspirated fluid into the chamber;

chamber outlet means, adapted for connection to the pump, for removing the introduced fluid from the chamber, said chamber outlet means being disposed along the housing longitudinal axis;

means, disposed in said console, for engaging and holding said housing, and chamber, with the longitudinal axis in a generally vertical orientation, with said chamber outlet means above said chamber inlet means, in order to promote rise of gas, in the introduced fluid, toward said chamber outlet means; and chamber shape means for directing rising gas, within the vertically oriented chamber, toward said chamber outlet means.

8. The apparatus according to claim 7 wherein the chamber inlet means and chamber outlet means are disposed on opposite sides of said chamber.

9. The apparatus according to claim 8 wherein said chamber has a perimeter and the apparatus further comprises means, orienting said chamber inlet means along the chamber perimeter, for causing circulation of the introduced fluid within said chamber in order to inhibit settling of particulate material, in the introduced fluid, in said chamber.

10. The apparatus according to claim 9 wherein said chamber has a generally circular shape.

11. The apparatus according to claim 10 further comprising diaphragm means, closing on side of said chamber, for enabling measurement of pressure of the introduced fluid.

12. The apparatus according to claim 9 wherein said chamber has a generally toroidal shape.

13. Fluid management apparatus for a surgical instrument having fluid irrigation and aspiration lines, said fluid management apparatus comprising:

a console having an aspiration pump;

a housing having a longitudinal axis and a chamber formed therein;

chamber inlet means, adapted for connection to the aspiration line, for introducing aspirated fluid into the chamber;

chamber outlet means, adapted for connection to the pump, for removing the introduced fluid from the chamber, said chamber outlet means being disposed along the housing longitudinal axis;

means, disposed in said console, for engaging and holding said housing, and chamber, to the console with the longitudinal axis in a generally vertical orientation, with said chamber outlet means below the pump, in order to promote rise of gas, in the introduced fluid, toward said chamber outlet means and thereafter into the pump; and chamber shape means for directing rising gas, within the vertically oriented chamber, toward said chamber outlet means.

14. The apparatus according to claim 13 wherein said chamber has a perimeter and the apparatus further comprises means, orienting said chamber inlet means along the chamber perimeter, for causing circulation of the introduced fluid within said chamber in order to inhibit settling of particulate material, in the introduced fluid, in said chamber.

15. The apparatus according to claim 14 wherein said chamber has a generally circular shape.

16. The apparatus according to claim 15 further comprising diaphragm means, closing one side of said chamber, for enabling measurement of pressure of the introduced fluid.

17. The apparatus according to claim 16 further comprising means, disposed in said housing, for enabling regulation of fluid through the irrigation and aspiration lines by plungers disposed in said console.

18. The apparatus according to claim 14 wherein said chamber has a toroidal shape.

19. A method for reducing expandable gas in the aspiration line of a fluid management system for a surgical instrument, the method comprising the steps of:

providing a console having an aspiration pump;

providing a housing having a longitudinal axis and a chamber with an aspiration fluid inlet and an aspiration fluid outlet, the outlet being disposed along the housing longitudinal axis;

connecting the outlet to the aspiration pump;

engaging and holding said housing and chamber to the console with the longitudinal axis in a vertical orientation with the fluid outlet disposed below the pump thereby enabling rise of gas, generated in or introduced into the chamber, from the chamber and into said aspiration pump; and providing said chamber with a shape for directing rising gas, within the vertically oriented chamber, toward said aspiration fluid outlet.

* * * * *